United States Patent
González Fernández et al.

(10) Patent No.: US 10,238,291 B2
(45) Date of Patent: Mar. 26, 2019

(54) METHOD FOR DIAGNOSING DENTAL DEMINERALIZATION PROCESSES

(71) Applicant: UNIVERSIDADE DE VIGO, Vigo (ES)

(72) Inventors: Pio Manuel González Fernández, Vigo (ES); Stefano Chiussi, Vigo (ES); Benigno Coello Delgado, Vigo (ES); Maria Rodríguez Domínguez, Vigo (ES); Miriam López Álvarez, Vigo (ES); Julia Serra Rodríguez, Vigo (ES)

(73) Assignee: UNIVERSIDADE DE VIGO, Vigo (ES)

( * ) Notice: Subject to any disclaimer, the term of this patent is extended or adjusted under 35 U.S.C. 154(b) by 0 days.

(21) Appl. No.: 15/568,372

(22) PCT Filed: Apr. 21, 2016

(86) PCT No.: PCT/ES2016/000049
§ 371 (c)(1),
(2) Date: Oct. 20, 2017

(87) PCT Pub. No.: WO2016/174280
PCT Pub. Date: Nov. 3, 2016

(65) Prior Publication Data
US 2018/0146857 A1 May 31, 2018

(30) Foreign Application Priority Data
Apr. 27, 2015 (ES) .................... 201500293

(51) Int. Cl.
*G01J 3/44* (2006.01)
*A61B 5/00* (2006.01)
(Continued)

(52) U.S. Cl.
CPC .............. *A61B 5/0075* (2013.01); *A61B 5/00* (2013.01); *A61B 5/0088* (2013.01); *A61B 6/14* (2013.01);
(Continued)

(58) Field of Classification Search
CPC ....... A61B 5/0075; A61B 5/00; A61B 5/0088; A61B 6/14; A61B 5/4547; A61B 2576/02; G01J 3/44
See application file for complete search history.

(56) References Cited

U.S. PATENT DOCUMENTS

2005/0283058 A1* 12/2005 Choo-Smith ........ A61B 5/0066
600/315

FOREIGN PATENT DOCUMENTS

WO WO 2009/012222 A1 1/2009

OTHER PUBLICATIONS

International Search Report and Written Opinion dated Jul. 8, 2016 for PCT/ES2016/000049, and English translation, 9 pages.
(Continued)

*Primary Examiner* — Jamil Ahmed
(74) *Attorney, Agent, or Firm* — Squire Patton Boggs (US) LLP

(57) ABSTRACT

The present invention relates to a quantitative ex vivo method for the complementary diagnosis of the degree of dental demineralization through the use of Raman spectroscopy, which comprises quantifying the intensities and areas of a plurality of Stoke bands of the spectrum, and defining and calculating indices that result from dividing the areas of certain bands of interest. The diagnosis is determined by the proximity of the values of these indices to the values previously obtained for the normal pattern of dental mineralization established by analyzing healthy dental parts. This method provides a complementary biomedical technique for
(Continued)

quantitative ex vivo analysis of the degree of dental demineralization on dental tissue remains extracted by medical prescription, and the information obtained will facilitate the prescription of suitable treatment to reduce or prevent said demineralization.

12 Claims, 2 Drawing Sheets

(51) Int. Cl.
    *A61B 6/14*     (2006.01)
    *G01N 21/65*     (2006.01)

(52) U.S. Cl.
    CPC ............... *G01J 3/44* (2013.01); *G01N 21/65* (2013.01); *A61B 5/4547* (2013.01); *A61B 2576/02* (2013.01)

(56) References Cited

OTHER PUBLICATIONS

Almond, L. Max, et al: "Raman spectroscopy: a potential tool for early objective diagnosis of neoplasia in the oesophagus", Biophotonics, Aug. 9, 2011, vol. 4(1), pp. 685-695.

Baelum, Vibeke "What is an appropriate caries diagnosis?", Acta Odontologica Scandinavica 2010, vol. 68, pp. 65-79.

Barman, Ishan, et al: "Selective sampling using confocal Raman spectroscopy provides enhanced specificity for urinary bladder cancer diagnosis", Anal Bioanal Chem Oct. 12, 2012, vol. 404(10), pp. 3091-3099.

Basting, Roberta Tarkany, et al: "Occlusal caries: diagnosis and noninvasive treatments", Quintessence International 1999, vol. 30(3), pp. 174-178.

De Carvalho, Fabiola Bastos, et al: "Use of laser fluorescence in dental caries diagnosis: a fluorescence x biomolecular vibrational spectroscopic comparative study", Brazilian Dental Journal 2013, vol. 24(1), pp. 59-63.

De Veld, D.C.G., et al: "Autofluorescence and Raman microspectroscopy of tissue sections of oral lesions", Lasers in Medical Science, Mar. 17, 2005, vol. 19, pp. 203-209.

Fejerskov, O. "Concepts of dental caries and their consequences for understanding the disease", Community Dentistry and Oral Epidemiology 1997, vol. 25(1), pp. 5-12.

Hanlon, E.B., et al: "Prospects for in vivo Raman spectroscopy", Physics in Medicine & Biology 2000, vol. 45(2), R1.

Harris, Andrew T., et al: "Raman spectroscopy and advanced mathematical modelling in the discrimination of human thyroid cell lines", Head & Neck Oncology, Oct. 29, 2009, vol. 1(38), pp. 1-6.

Hughes, O.R., et al: "Optical and molecular techniques to identify tumor margins within the larynx", Head & Neck Nov. 2010, vol. 32(11), pp. 1544-1553.

Jerjes, W., et al: "Detection of cervical intranodal metastasis in oral cancer using elastic scattering spectroscopy", Oral Oncology 2004, vol. 40(7), pp. 673-678.

Ko, A. C.-T., et al: "Application of NIR Raman spectroscopy for detecting and characterizing early dental caries", Biomedical Vibrational Spectroscopy III: Advances in Research and Industry, 2006, Proceedings of SPIE 2006, 6093, Article No. 60930L, pp. 60930L-1-60930L-10.

Ko, Alex C.-T., et al: "Detection of early dental caries using polarized Raman spectroscopy", Optics Express Jan. 9, 2006, vol. 14(1), pp. 203-215.

Ko, Alex C.-T., et al: "Ex vivo detection and characterization of early dental caries by optical coherence tomography and Raman spectroscopy", Journal of Biomedical Optics May 26, 2005, vol. 10(3), Article No. 031118, pp. 031118-1-031118-16.

Li, Yi, et al: "Research on the Raman spectral character and diagnostic value of squamous cell carcinoma of oral mucosa", Journal of Raman Spectroscopy, Aug. 19, 2009, vol. 41(2), pp. 142-147.

Medina, Juan Carlos, et al: "Evaluacion de los metodos de diagnostic en la deteccion de la caries dental por odontologos venezolanos", Acta Odontologica Venezolana Caracas 2006, Mar. 29, 2005, pp. 1-11.

Mohanty, B., et al: "Characterizing and identifying incipient carious lesions in dental enamel using micro-raman spectroscopy", Oct. 10, 2012, Caries Research 2013, vol. 47(1), pp. 27-33.

Petersen, Poul Erik, "World Oral Health Report 2003", World Health Organization Geneva, Switzerland, http://www.who.int/oral_health/publications/report03/en/).

Pitts, Nigel, et al. "Clinical diagnosis of dental caries: A European Perspective", Journal of Dental Education Oct. 2001, vol. 65(10), pp. 972-979.

Salehi, Hamideh, et al: "Functional mappinog of human sond and carious enamel and dentin with Raman spectroscopy", Journal of Biophotonics Sep. 20, 2012, vol. 6(10), pp. 764-774.

Stone, Nicholas, et al: "Near-infrared Raman spectroscopy for the classification of epithelial pre-cancers and cancers", Journal of Raman Spectroscopy 2002, vol. 33(7), pp. 564-573.

Stone, Nicholas, et al: "Raman spectroscopy for early detection of laryngeal malignancy: preliminary results", The Laryngoscope, Oct. 2000, vol. 110, pp. 1756-1763.I.

Tu, Qiang, et al: "Diagnostic applications of Raman spectroscopy", Nanomedicine: Nanotechnology, Biology, and Medicine 2012, vol. 8(5), pp. 545-558.

Valdes, Roberto, et al: "Pilot research on the evaluation and detection of head and neck squamous cell carcinoma by Raman spectroscopy", Journal of Raman Spectroscopy, May 27, 2014, vol. 45(7), pp. 550-557.

Veitia, Lizmar D., et al: "Metodos convencionales y no convencionales para la deteccion de lesion inicial de caries", Acta Odontologica Venezolana 2011, vol. 49(2), pp. 1-14.

\* cited by examiner

METHOD FOR DIAGNOSING DENTAL DEMINERALIZATION PROCESSES

This application is a national phase application of PCT/ES2016/000049 filed on Apr. 21, 2016, which claims priority to ES P201500293 filed on Apr. 27, 2015, the contents of which are incorporated by reference in their entirety.

TECHNICAL FIELD

The present invention is part of the field of biomedical instrumentation and, more specifically, the sector of dentistry. Its foundation, based on Raman spectroscopy, makes it possible to quantitatively assess the composition of mineralized tissues. In particular, the ex vivo analysis of dental tissue remains (tartar, enamel, dentin) extracted by medical prescription by way of biopsy will make it possible to quantify the degree of dental demineralization of said tissue. This objective and quantitative information is of great importance to complement the knowledge about the oral health state of the patient, which will facilitate the diagnosis and prescription of treatments according to the degree of dental demineralization obtained, in order to prevent or reverse said dental demineralization and, therefore, other derived ailments, emphasizing caries as the most prevalent disease.

BACKGROUND

Dental caries is defined as a dynamic process caused by an imbalance between the mechanisms of demineralization and remineralization as a result of microbial metabolism, and the effects of this imbalance on hard tissues of the tooth (Fejerskov O. Concepts of dental caries and their consequences for understanding the disease. Community Dentistry and Oral Epidemiology 1997; 25(1): 5-12). Currently, these dental demineralization processes are a significant oral health problem, especially in the most industrialized countries wherein it is the disease with the highest prevalence and incidence in the population, largely affecting schoolchildren (60-90%) and the vast majority of adults (Petersen P. E. World Oral Health report 2003. World Health Organization Geneva, Switzerland. http://www.who.int/oral_health/publications/report03/en/).

To apply the least aggressive treatment possible and to ensure good oral health, early diagnosis of these demineralization processes is essential. Currently, in the clinic, most caries are diagnosed in their initial phases during routine visual checks, tactile exploration with probes and dental X-rays. This combined methodology improves the detection of caries, providing greater X-ray sensitivity (with 66%) in comparison to visual and tactile checks (with 52%), and, on the other side, greater specificity in visual and tactile checks (with 98%) in comparison to X-ray checks (with 95%), according to Baelum (V. Baelum, What is an appropriate caries diagnosis?. Acta Odontologica Scandinavica, 68, pp 65-79, 2010).

In searching for improvements related to efficiency in diagnosing early lesions, there are other less conventional diagnostic methods, such as fiber-optic transillumination, electrical conductivity measurements and laser fluorescence methods (Medina J. C., Salgo N., Acevedo A. M. Assessment of the diagnostic methods for detecting dental caries by Venezuelan dentists. Acta Odontologica Venezolana, 2, Caracas, 2006). These techniques provide some improvements with respect to conventional X-rays, however, they still cannot substitute them. For example, in the case of transillumination, it is not possible to take pictures below the gingival margin nor precise measurements of the depth of the proximal lesion. In the case of electrical conductivity measurements, there are a many variables that the final value of resistance to the electrical conductivity of each tooth will depend on, such as porosity, volume of saliva in the area of concentration, temperature and ion concentration. Therefore, it is a technique with high variability and specificity lower than the visual check wherein the clinical evaluation time has not yet been optimized. Lastly, with regard to the laser fluorescence methods, it has been demonstrated that the size of the lesion alters the level of fluorescence, which determines the quantified value, leading to a high number of false positives in diagnosed cases, such as hypomineralization due to dental caries in cases of developing teeth. Finally, there are also the so-called techniques of multiphoton imaging, infrared thermography and optical coherence tomography which are other diagnostic research methods used today (Lizmar D. Veitia E., Acevedo A. M, Rojas Sanchez F. Bibliographic Reviews: Conventional and non-conventional methods for detecting initial caries lesions. Acta Odontologica Venezolana, 2011, 49(2), 1-14).

Despite all of these advances, it is important to note that the visual check followed by x-rays is still considered the most effective method for the in vivo diagnosis (Lizmar et. al. 2011, vide supra). However, given the lack of improvements related to specificity, it would interesting to be able to determine the extent of the affected tissue and the degree of activity of the lesion, as well as a greater degree of sensitivity to detect dental demineralization in the first stages, and not only provide dichotomous responses (presence/absence of the disease) as occurs now (Takany Basting R and Campos Serra M. Occlusal caries: Diagnosis and noninvasive treatments. Quintessence Int. 30, pp 174-178, 1999; Nigel B. Pitts. Clinical Diagnosis of Dental Caries: A European Perspective. Journal of Dental Education, 10, pp 972-979, 2001). Furthermore, the development of complementary biomedical technologies that allow for the ex vivo study of the composition of dental tissue already extracted from the patent by medical prescription is also of great interest to complement the diagnosis of the dental health of the patient and thus be able to encourage treatments to prevent or reduce diseases accordingly.

Raman Spectroscopy

Raman spectroscopy is a photonic analytical technique with a high spatial resolution that is fundamentally based on exciting a target tissue with a monochromatic laser and subsequently recording the inelastic light scattering, which constitutes Raman radiation. This inelastic scattering makes it possible to obtain information about the molecular vibrations by measuring the differences between the energy of the incident photons and that of the scattered photons. For example, due to the fact that diseases and other pathological ailments lead to chemical and structural changes, vibration changes are observed in the Raman spectra which can be used as phenotypic markers, sensitive to the disease.

In fact, the peaks in the Raman spectrum from 400 to 1800 $cm^{-1}$ have been correlated with the molecular vibrations considered to be biochemically relevant for certain diseases or other pathological ailments wherein chemical and structural changes are produced. Said changes can therefore be quantified in the Raman spectrum and used as a phenotypic marker, sensitive to each disease like a molecular fingerprint of the target tissue, determined by the type of specific molecular vibrations of the chemical bonds of the nucleic acids, lipids and biological proteins. These chemical bonds assessed by Raman spectroscopy will consist of narrow vibration peaks in certain spectral regions, as compared to the largely unspecific broad profiles of emission and low resolution obtained, for example, by means of fluorescence methods (Hughes O. R., N. Stone, M. Kraft, C. Arens, M. A. Birchall, Head Neck 2010; 32(11), 1544; Li Y., Z. N. Wen, L. J. Li, M. L. Li, N. Gao, Y. Z. Guo, J. Raman Spectrosc. 2010; 41(2), 142; Stone N., C. Kendall, N. Shepherd, P. Crow, H. Barr, J. Raman Spectrosc. 2002; 33(7), 564).

The collection or gathering of Raman spectra does not disturb the cellular environment and this spectroscopy is capable of detecting minor alterations in the biochemical composition of living cells and providing a diagnostic molecular fingerprint of the target tissue (Valdés R., Stefanov S., Chiussi S., López-Álvarez M., González P. Pilot research on the evaluation and detection of head and neck squamous cell carcinoma by Raman spectroscopy. Journal of Raman Spectroscopy 45(7), 2014, 550-557). Likewise, this methodology does not require special preparation of the sample nor markers, the presence of water does not distort the analysis, the spectrum is acquired quickly and the intensity of the Raman band is directly proportional to the concentration. Given all these advantages, over the last decade important technological advances have been made in spectrometry as well as in computing techniques that have made it possible to make significant progress in Raman spectroscopy applied to biological and life sciences (D C de Veld D C., Bakker Schut T C., Skurichina M., Witjes M J., Van der Wal J E., Roodenburg J L., Sterenborg H J. Lasers Med Sci 2005, 19(4):203-9], [N Stone, MSc (Dist.); Pela Stavroulaki, M D; Catherine Kendall, MSc (Dist.); Martin Birchall, M D; Hugh Barr, M D (Dist.). Laryngoscope, 110:1756-1763, 2000] [Harris A T., Garg M., Yang X B., Fisher S E., Kirkham J., Smith D A., Martin-Hirsch D P., High A S.: Raman spectroscopy and advanced mathematical modelling in the discrimination of human thyroid cell lines. Head Neck Oncol 2009, 1(1): 38).

Raman Spectroscopy in Dentistry

Raman spectroscopy has been researched for decades as a diagnostic tool for characterizing the early malignant changes that occur in the upper gastrointestinal tract, as well as in a range of other tissues, including the bladder, breast, bone, lung, blood, lymph nodes, larynx and stomach (Jerjes W., B. Swinson, D. Pickard, G. J. Thomas, C. Hopper, Oral Oncol. 2004; 40(7), 673; Almond L. M., J. Hutchings, N. Shepherd, H. Barr, N. Stone, C. Kendall, J. Biophoton. 2011; 4(10), 685; Barman I., N. C. Dingari, G. P. Singh, R. Kumar, S. Lang, G. Nabi, Anal. Bioanal. Chem. 2012; 404(10), 3091; Hanlon E. B., R. Manoharan, T. W. Koo, K. E. Shafer, J. T. Motz, M. Fitzmaurice, J. R. Kramer, I. Itzkan, R. R. Dasari, M. S. Feld, Phys. Med. Biol. 2000; 45(2), 1; Tu Q., C. Chang, Nanomedicine 2012; 8(5), 545). However, clinical studies in hard mineralized tissue continue to be few; despite the high level of sensibility, in terms of detecting structural changes at a molecular level in the mineralized tissues, such as phenotypic markers in a determined disease with a specific chemical, Raman spectroscopy emerges as a powerful diagnostic tool for detecting and assessing the degree of dental demineralization.

Thus, among the few works focused on mineralized tissues, Ko et. al. (2005) (Ko A C T, Choo-Smith L P., Hewko M., Leonardi L., Sowa M G., Dong C C S., Williams P., Cleghorn B. Ex vivo detection and characterization of early dental caries by optical coherence tomography and Raman spectroscopy. Journal of Biomedical Optics 2005, 10(3), Article number 031118) published ex vivo detection and characterization of early dental caries by combining optical coherence tomography (OCT) and Raman spectroscopy, providing images to detect caries and determine the depth of the lesion and, through Raman spectroscopy, the obtained biochemical confirmation of the caries. The same authors, Ko et. al. (Ko A C T., Choo-Smith, L P., Hewko M., Sowa M G., Dong C C S, Cleghorn B. Detection of early dental caries using polarized Raman spectroscopy. Optics Express 2006, 14(1), 203-215) published the detection of early dental caries in extracted human teeth by using polarized Raman spectroscopy to distinguish between early dental caries and healthy enamel. Finally, Ko et. al. (Ko A C T., Choo-Smith L P., Zhu R., Hewko M., Dong C., Cleghorn B., Sowa M G. Application of NIR Raman spectroscopy for detecting and characterizing early dental caries. Progress in Biomedical Optics and Imaging-Proceedings of SPIE 2006, 6093, Article number 60930L) also published the application of NIR Raman spectroscopy for detecting and characterizing early dental caries in extracted human teeth wherein the excitation laser of the near I R provided the biochemical contrast.

Mohanty et. al. (Mohanty B., Dadlani D., Mahoney D., Mann A B. Characterizing and identifying incipient carious lesions in dental enamel using micro-Raman spectroscopy. Caries Research 2013, 47(1), 27-33) characterized and identified ex vivo cases of incipient caries (grown on human molars under controlled exposure to lactic acid) in dental enamel using micro-Raman spectroscopy to conclude that said spectroscopy has both requirements of sensitivity and selectivity to identify incipient carious lesions; however, the presence of a surface layer with a relatively high mineral content could complicate the analysis. Carvalho et. al. (Carvalho F. B., Barbosa A F S., Zanin F A A., Brugnera Jinior A., Silveira Júnior L., Pinheiro A L B. Use of laser fluorescence in dental caries diagnosis: A fluorescence x biomolecular vibrational spectroscopic comparative study. Brazilian Dental Journal 2013, 24(1), 59-63) researched the ex vivo use of laser fluorescence in dental caries diagnosis to verify the existence of a correlation between the readings of the Raman spectroscopy of the levels of apatite phosphate groups (~960 cm$^{-1}$), fluorinated apatites (~575 cm$^{-1}$) and an organic matrix (~1450 cm$^{-1}$) in different phases of dental caries in extracted human teeth. Finally, Salehi et. al. (Salehi H., Terrer E., Panayotov I., Levallois B., Jacquot B., Tassery H., Cuisinier F., Functional mapping of human sound and carious enamel and dentin with Raman spectroscopy. Journal of Biophotonics 2013, 6(10), 765-774) carried out ex vivo functional mapping of extracted human teeth, specifically human enamel and carious enamel and dentin, with Raman spectroscopy through a precise analysis of the variations of the spectrum of the Raman band for minerals and organic components.

All of these research projects carried out on ex vivo dental tissues by way of biopsy validate the interest of the present invention with regard to the potential of Raman spectroscopy as a complementary clinical tool for diagnosing dental demineralization. However, they all propose the use of this technology with a qualitative focus with regard to the identification of functional groups of interest in mineralized tissues. This means that the potential implementation of Raman in the clinic would still require a significant amount of time to evaluate the spectra and, once evaluated, a numerical index of the potential degree of demineralization of the analyzed dental tissue remains would not be obtained.

Description of the Invention

The relevant aspect of the present invention relates to the proposal of an ex vivo method for the quantitative assessment of the degree of dental demineralization by means of Raman spectroscopy, characterized by:

1. Quantifying in the Raman spectrum, obtained after irradiating the dental part with laser light, the areas of the Stokes bands associated with the groups: $PO_4^{-3}$ bending of hydroxyapatite (430 cm$^{-1}$), $PO_4^{-3}$ stretching of hydroxyapatite (960 cm$^{-1}$) and the C—H$_x$ lipid and protein group (2941 cm$^{-1}$) and calculating the values of the following relative indices defined for the diagnosis:

Index Mineralization bending(IMb): $PO_4^{-3}$ band area at 430 cm$^{-1}$/C—H$_x$ band area at 2941 cm$^{-1}$.

Index Mineralization stretching (IMs): $PO_4^{-3}$ band area at 960 cm$^{-1}$/C—H$_x$ band area at 2941 cm$^{-1}$.

2. Determining the diagnosis by the proximity of the values obtained with the normal pattern for the levels of mineralization of the healthy dental part, established at 1.35-1.75 for IMb and 4.01-5.19 for IMs.

To estimate the indices, healthy dental parts were analyzed and the random error derived from the measuring process, as well as the systematic error derived from fluctuations inherent to the equipment due to variations in the topography of the sample, were taken into account. Healthy human dental parts as well as those affected with different degrees of caries used to establish the indices of the present invention were extracted by medical instruction after the diagnosis of periodontal and wisdom tooth disease.

Another aspect of the invention relates to the different ways of taking the sample. The ex vivo sample preparation allows for laboratory examination using conventional Raman equipment. Ex vivo is to be understood as the analysis of dental tissue samples obtained, by medical prescription for other pathologies, by way of biopsy through currently standardized techniques in the dental practice, such as dental microbiopsy through acid etching, cuts by abrasion with sof-lex discs or fragments in the case of using cuts of dental enamel with instruments or rotation, and lastly, dental extraction (in this final case, it is not a generalized technique since it is not harmless, unlike the other preceding techniques).

This method can use a variety of laser types that emit in the visible range, such as the He—Ne laser (632 nm), diode laser (637 nm, 785 nm) or similar, and radiation-emitting lasers in the ultraviolet range (usually 488 or 532 nm) or the near infrared range, such as the Nd:YAG laser (1064 nm).

In another aspect of the invention, the present method is applicable as a complementary technique to different types of diseases that affect hard tissues of the tooth, starting with dental caries but also including fluorosis or amelogenesis imperfecta (AI), since all three lead to changes in the ultrastructure and in the ratios of the different tooth compounds (organic compared to the mineral part). This method is especially applicable to the ex vivo diagnosis of early dental demineralization, without external signs that indicate its presence, such that it will facilitate the diagnosis thereof, which is currently difficult with the in vivo routine techniques.

In another aspect of the invention, the present method can be implemented by computer or other electronic means, in addition to software designed to immediately calculate the established mineralization indices and thus facilitate and streamline the processing of the diagnostic information.

The Raman spectrum of enamel and dentin in healthy human teeth (FIG. 1) and the lineal relationship proven between the band areas of interest with respect to the incident laser radiation (FIG. 2) are presented at the end of this document.

DETAILED DESCRIPTION OF THE INVENTION

Practical Cases

In a particular embodiment, two dental parts with a different external appearance of demineralization: upper molar (FIG. 3(a)) and upper premolar (FIG. 3(b)), extracted from two patients by medical instruction after the diagnosis of periodontal disease due to having high mobility, were evaluated by Raman spectroscopy. Both figures show the ex vivo dental parts analyzed from different angles: oral, occlusal and longitudinal cross section in detail.

Figure 1:
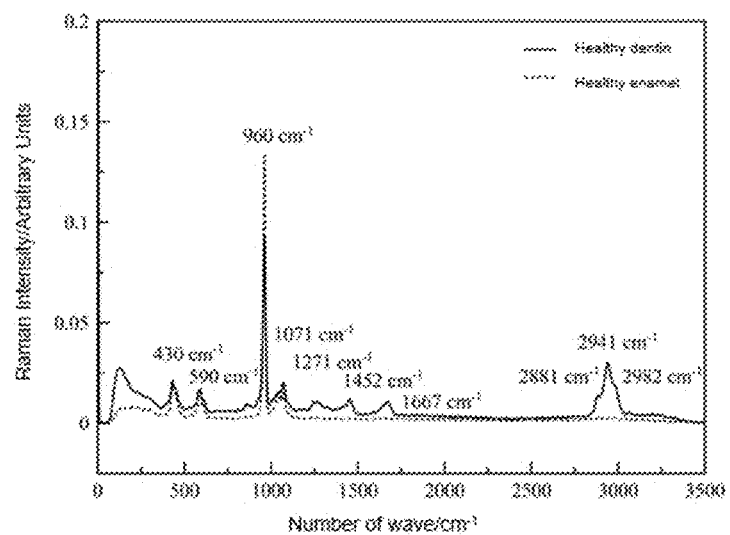
FIG. 1. Raman spectrum of enamel and dentin in healthy human teeth. Extracted by medical instruction after the diagnosis of periodontal disease due to having high mobility.
Figure 2:
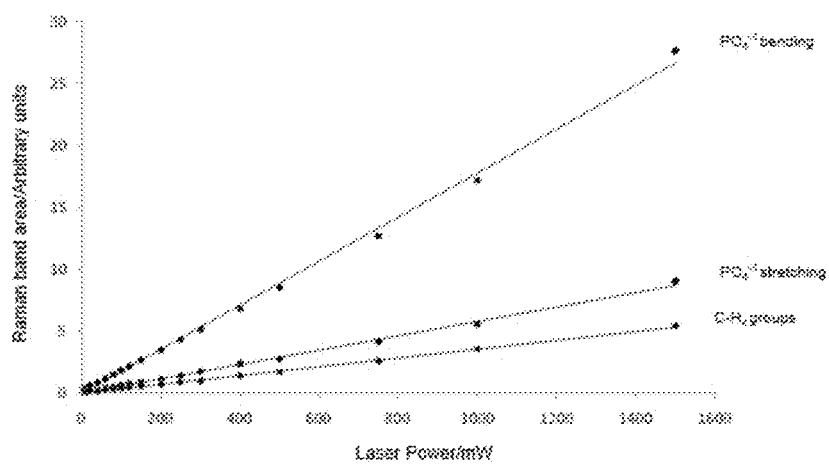
FIG. 2. Lineal relationship between the Raman bands of interest ($PO_4^{-3}$ bending at 430 cm$^{-1}$, $PO_4^{-3}$ stretching at 960 cm$^{-1}$ and C—H$_x$ lipid and protein groups at 2941 cm$^{-1}$) with respect to incident laser radiation.
Figure 3:
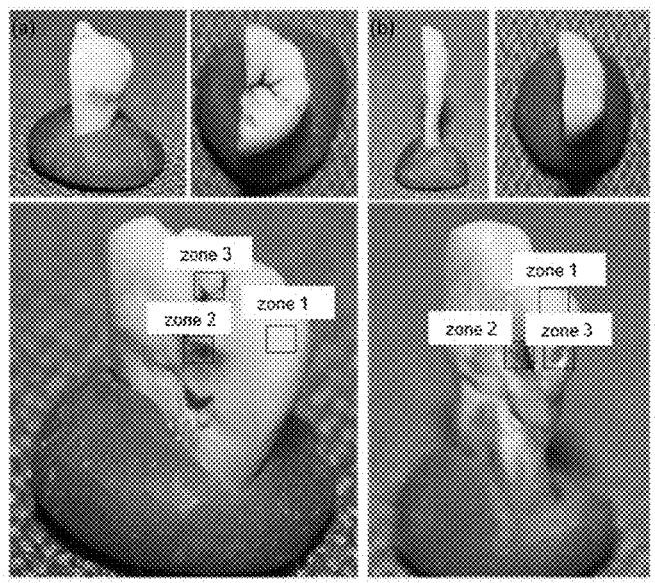
FIG. 3. Longitudinal cross section of an upper molar (a) and an upper premolar (b) affected by dental caries obtained from two patients for the assessment thereof by the present quantitative method of Raman spectroscopy. Dental parts extracted by medical instruction after diagnosis of periodontal disease due to having high mobility.
Figure 4:
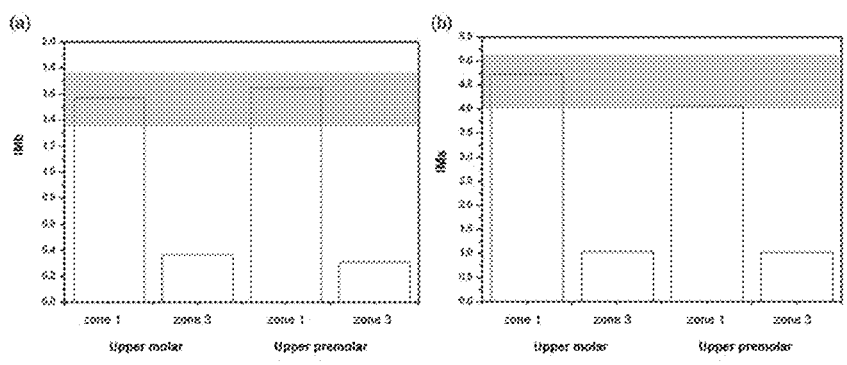
FIG. 4. Quantitative results obtained for the case studies, wherein (a) has IMb values for zones 1 (healthy enamel) and 3 (carious enamel or potentially affected without clear evidence) of the upper molar and upper premolar, respectively. The gray shaded area represents the normal pattern. The graph (b) is the same study but for the IMs index. Dental parts extracted by medical instruction after diagnosis of periodontal disease due to having high mobility.

In the images of the upper molar (FIG. 3(a)), clear external signs of dental demineralization are observed. In the case of the premolar tooth (FIG. 3(b)), it presents inner demineralization without clear external signs of an imbalance in demineralization and dental caries, which would make it possible to assess the depth of detection of the Raman signal in the tissue. By providing a longitudinal cross section, the inner dental caries can be observed. Thus, zone 1 of FIG. 3 corresponds in both cases to the healthy enamel, zone 2 to the dentin affected by caries and zone 3 to the external area of interest to be assessed by the quantitative Raman methodology by indices.

As a preferred embodiment, the following method is described for diagnosing dental demineralization in zones without external evidence:

1. Selection of those dental tissue remains extracted by medical instruction following the diagnosis of different pathologies and with certain suspicions of imbalances in the mineralization given by the diagnosis but without clear external evidence.
2. Analysis of the surface of these dental parts (FIGS. 3(a) and (b)) using Raman spectroscopy to obtain the corresponding spectra.
3. Obtaining, for each spectrum in the external zones (zone 1 and zone 3 for the two dental parts), the Raman band areas at 430 cm$^{-1}$, 960 cm$^{-1}$ and 2941 cm$^{-1}$.
4. From the Raman band areas of interest, the mineralization indices (IMb and IMs) are obtained for each zone. These indices for the practical case proposed are as follows:

|  | Upper molar | | Upper premolar | |
| --- | --- | --- | --- | --- |
|  | IMb | IMs | IMb | IMs |
| Zone 1 | 1.571 | 4.735 | 1.651 | 4.069 |
| Zone 3 | 0.369 | 1.039 | 0.312 | 1.030 |

5. The indices obtained for the zones of interest (zone 3 in both cases) are compared to the values assigned to the normal pattern with respect to the mineralization obtained from the study of the healthy dental parts, and established at: 1.35-1.75 for IMb and 4.01-5.19 for IMs. A diagnosis is created to compare the values of these indices to the normal parameters.

The results obtained for the case studies using the proposed mineralization indices clearly validate Raman spectroscopy, as well as the normal pattern established for the levels of mineralization in healthy enamel, as a complementary quantitative technique that is reliable, objective and self-sufficient for diagnosing dental demineralization with high levels of specificity and sensitivity both on a surface level as well as in inner tissues of the teeth. This methodology can be easily transferred to the clinic for the application thereof in extracted dental parts of patients as a quantitative and objective complement to the diagnosis in order to apply future treatments according to the quantified degree of dental demineralization. In this way, the mineralization indices of the ex vivo dental parts object of study are obtained almost in real time, and their correspondence with the confidence interval or normal pattern for health states of dental mineralization are checked. The early diagnosis of demineralization processes is essential to be able to apply the least aggressive treatment possible and to ensure good oral health. This methodology will make it possible to categorize the degree of mineralization of dental parts with a quantitative approach even in incipient caries or those that are not clearly shown externally in order to prescribe preventative treatments to the patient according to the quantified degree of mineralization.

The invention claimed is:

1. A quantitative ex vivo method for diagnosing dental demineralization processes by Raman Spectroscopy characterized by:

quantifying in the Raman spectrum obtained after irradiating the dental part with laser light, the areas of the Stokes bands associated with $PO_4^{-3}$ bending of hydroxyapatite (430 $cm^{-1}$), $PO_4^{-3}$ stretching of hydroxyapatite (960 $cm^{-1}$) and the $C-H_x$ lipid and protein group (2941 $cm^{-1}$) and calculating the following relative indices defined for the diagnosis:

Mineralization Index bending (IMb)=band area 430 $cm^{-1}$/band area 2941 $cm^{-1}$;

Mineralization Index stretching (IMs)=band area 960 $cm^{-1}$/band area 2941 $cm^{-1}$;

determining the diagnosis by the proximity of the values of said indices with the values previously established as the normal pattern with respect to the mineralization of healthy dental parts, established at: 1.35-1.75 for IMb and 4.01-5.19 for IMs.

2. The quantitative ex vivo method for diagnosing dental demineralization processes by Raman Spectroscopy according to claim 1, characterized by the fact that said method is implemented by computer.

3. The method according to claim 1, which is used for the complementary diagnosis of demineralization processes associated with dental caries.

4. The method according to claim 1, which is used for the complementary diagnosis of dental demineralization processes that alter the formation and calcification of the tooth.

5. The method according to claim 2, which is used for the complementary diagnosis of demineralization processes associated with dental caries.

6. The method according to claim 2, which is used for the complementary diagnosis of dental demineralization processes that alter the formation and calcification of the tooth.

7. The method according to claim 3, which is used for the complementary diagnosis of dental demineralization processes that alter the formation and calcification of the tooth.

8. The method according to claim 5, which is used for the complementary diagnosis of dental demineralization processes that alter the formation and calcification of the tooth.

9. The method according to claim 4, wherein the dental demineralization processes that alter the formation and calcification of the tooth are selected from fluorosis and amelogenesis imperfecta (AI).

10. The method according to claim 6, wherein the dental demineralization processes that alter the formation and calcification of the tooth are selected from fluorosis and amelogenesis imperfecta (AI).

11. The method according to claim 7, wherein the dental demineralization processes that alter the formation and calcification of the tooth are selected from fluorosis and amelogenesis imperfecta (AI).

12. The method according to claim 8, wherein the dental demineralization processes that alter the formation and calcification of the tooth are selected from fluorosis and amelogenesis imperfecta (AI).

* * * * *